(12) United States Patent
Haerder et al.

(10) Patent No.: US 9,010,323 B2
(45) Date of Patent: Apr. 21, 2015

(54) INHALER AND SIEVE FOR AN INHALER

(75) Inventors: Lukas Haerder, Bad Neustadt/Saale (DE); Claus Breuer, Ennigerloh (DE)

(73) Assignee: Boehringer Ingelheim Pharma GmbH & Co. KG, Ingelheim am Rhein (DE)

( * ) Notice: Subject to any disclaimer, the term of this patent is extended or adjusted under 35 U.S.C. 154(b) by 404 days.

(21) Appl. No.: 12/921,447

(22) PCT Filed: Mar. 11, 2009

(86) PCT No.: PCT/EP2009/052858
§ 371 (c)(1),
(2), (4) Date: Oct. 11, 2010

(87) PCT Pub. No.: WO2009/112521
PCT Pub. Date: Sep. 17, 2009

(65) Prior Publication Data
US 2011/0120465 A1 May 26, 2011

(30) Foreign Application Priority Data
Mar. 13, 2008 (DE) .......................... 10 2008 014 025

(51) Int. Cl.
*A61M 15/00* (2006.01)
*A61M 11/00* (2006.01)
(Continued)

(52) U.S. Cl.
CPC ..... *A61M 15/0028* (2013.01); *A61M 2202/064* (2013.01); *A61M 11/003* (2013.01); *A61M 15/0026* (2013.01); *A61M 15/003* (2013.01); *A61M 15/0035* (2013.01)

(58) Field of Classification Search
CPC ........ B01D 39/12; B01D 71/024; B01D 9/12; B01D 7/02; B01D 39/1623; B60R 21/2644; A61M 2202/064; A61M 15/0028; A61M 16/0808; A62B 7/02; A62B 9/04; A62B 7/10; A62B 23/025; A41D 13/11
USPC ............. 128/200.18, 203.19, 203.21; 96/362, 96/363; 222/189.09
See application file for complete search history.

(56) References Cited

U.S. PATENT DOCUMENTS 2,380,182 A * 7/1945 La Bille .................... 128/203.23
2,456,621 A * 12/1948 Cheney, Jr. .................... 264/127
(Continued)

FOREIGN PATENT DOCUMENTS

CA 2507579 A1 6/2004
DE 8801555 U1 6/1988
(Continued)

OTHER PUBLICATIONS

International Search Report for PCT/EP2009/052828 mailed Jun. 6, 2009.
(Continued)

*Primary Examiner* — Tan-Uyen (Jackie) T Ho
*Assistant Examiner* — Mark Wardas
(74) *Attorney, Agent, or Firm* — Michael P. Morris; Wendy A. Petka

(57) ABSTRACT

An inhaler (1) includes a sieve part (9) for administrating powdered substances such as medical substances. The inhaler (1) includes a suction air channel (6) leading to a mouthpiece (4), a substance supply container (8) that is moveable inside a receiving chamber (7) and the sieve part (9) disposed in the suction air channel (6) between the receiving chamber (7) and the mouthpiece (4). The sieve part includes a retaining edge (10), a sieve area contained in a cross sectional area within the retaining edge (10), and a protruding area (12) that protrudes to one side and has a flat portion (13).

22 Claims, 4 Drawing Sheets

(51) Int. Cl.
*A61M 16/00* (2006.01)
*B05D 7/14* (2006.01)
*B65D 83/06* (2006.01)

(56) References Cited

U.S. PATENT DOCUMENTS

| | | | |
|---|---|---|---|
| 2,741,319 A * | 4/1956 | Mickelsen | 169/87 |
| 3,483,980 A | 12/1969 | Cochran | |
| 3,499,677 A * | 3/1970 | Callon et al. | 296/170 |
| 4,846,168 A * | 7/1989 | Abiko et al. | 128/203.15 |
| 4,918,017 A | 4/1990 | Greenstreet et al. | |
| 4,995,385 A * | 2/1991 | Valentini et al. | 128/203.21 |
| 5,401,406 A * | 3/1995 | Johnson et al. | 210/323.2 |
| 5,460,173 A * | 10/1995 | Mulhauser et al. | 128/203.15 |
| 5,582,205 A * | 12/1996 | McCarty et al. | 137/545 |
| 5,647,347 A * | 7/1997 | Van Oort | 128/203.15 |
| 6,250,301 B1 * | 6/2001 | Pate | 128/203.26 |
| 7,025,059 B2 * | 4/2006 | Pera | 128/203.21 |
| 7,669,617 B2 * | 3/2010 | Parks et al. | 141/241 |
| 2002/0158150 A1 | 10/2002 | Matsugi et al. | |
| 2004/0149283 A1 * | 8/2004 | Hochrainer | 128/203.15 |
| 2009/0277446 A1 * | 11/2009 | Walz | 128/203.15 |
| 2010/0269819 A1 * | 10/2010 | Sievers et al. | 128/200.23 |

FOREIGN PATENT DOCUMENTS

| | | |
|---|---|---|
| DE | 102006016904 A1 * | 10/2007 |
| GB | 2253200 A | 9/1992 |
| WO | 9747347 A1 | 12/1997 |
| WO | 2004047796 A2 | 6/2004 |
| WO | 2007118801 A1 | 10/2007 |

OTHER PUBLICATIONS

Abstract in English for DE8801555, downloaded from espacenet Sep. 7, 2010.

* cited by examiner

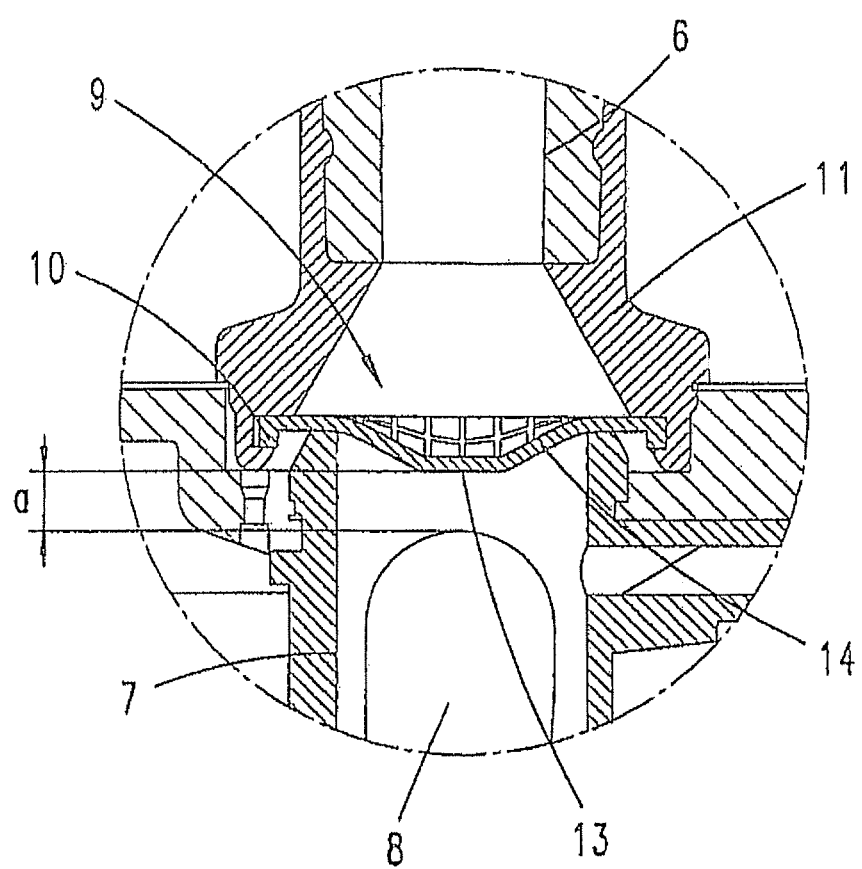

INHALER AND SIEVE FOR AN INHALER

The invention relates first of all to an inhaler for powdered, in particular medicinal substances, having a suction air channel leading to a mouthpiece, furthermore a substance supply container preferably movably arranged in a receiving chamber, and a sieve part disposed in the suction air channel between the receiving chamber and the mouthpiece, said sieve part having a retaining edge and a sieve area contained in a cross-sectional area within the retaining edge, wherein the sieve area comprises a protruding area that protrudes to one side.

Inhalers of this kind are known. Reference is made for example to WO 2004/062716 A1. The sieve part delimits the receiving chamber on one side, in the direction of the mouthpiece. However, in view of the requirement for very accurate dimensions of the receiving chamber, which in turn are connected with the desired mobility of the substance supply container, the sieve part is subject to stringent demands as to the maintenance of its precise dimensions. In a sieve part corresponding to the in-house prior art of the Applicant, a dome-shaped convexity is provided as the protruding area. The convexity is designed to face the substance supply container. However, it has been found that from a manufacturing point of view it is very difficult to achieve the dimensional tolerances required.

Starting from the prior art shown, the invention is concerned with the problem of providing an inhaler the sieve part of which is of advantageous design.

One possible solution to the problem is provided by the subject-matter of claim 1, according to a first inventive idea, while in this instance the crucial feature is that the protruding area has a flat portion. Surprisingly it has been found that, with a view to increasing the dimensional stability, it is indeed possible to construct a protruding area in the sieve area of the sieve part, but that the dimensional stability can be improved substantially more if this protruding area has a flat portion. Thus, the protruding area is not continuously dome-shaped. Rather, the protruding area grows out of the surrounding sieve area but then bends at an angle, so to speak, in cross-sectional view, to form a flat portion.

Further features of the invention are explained hereinafter, including in the description of the drawings, often in their preferred association with the claim concept mentioned above. However, they may also be associated with only one or with several of the individual features of this claim or may be of significance independently or in another overall concept.

Thus, first of all, it is preferred that the protruding area, when viewed in cross-section, should project over the retaining edge at right-angles to a plane extending through the retaining edge.

The retaining edge as such may have an angular bend. The bend may be in the direction of the protruding area but may also be in the opposite direction. The bend is formed by an outermost edge portion of the sieve part. The sieve part may be made as a whole from a flat wire mesh part by bending or deep drawing, with at least partial plastic deformation.

It is also preferred that the flat portion, when viewed in cross-section, should be in the centre of the sieve part. This central arrangement relates in particular to a sieve part which has a circular overall plan view. However, in the case of an angular plan view, this may also be arranged surrounding the centre provided.

The flat portion as such has a dimension, based on a cross-sectional representation, that corresponds to part of the overall free spacing between opposing regions of the retaining edge. In the case of a circular diameter, therefore, it corresponds to part of a diameter thus formed. This partial area preferably corresponds to 5% or more of the sieve clamped within the retaining edge. This is specifically in relation to a projection of a line that directly connects the opposing regions of the retaining edge to one another. In the case of a rectangular plan view, this measurement relates initially to the smallest dimension between opposing regions of the retaining edge. Also preferably, the dimension is less than 15% of the total dimension of the above-mentioned cross-sectional line. Where there is a restriction to the area now defined by the upper and lower limits, all the intermediate values relating to this area are also included in the disclosure, specifically in increments of $\frac{1}{10}$%. The dimensions stated relate to an overall dimension of the sieve area in the exposed, clamped area under discussion of between 5 and 15 mm. Here, again, all the related intermediate values are also included in the disclosure, particularly in increments of $\frac{1}{10}$ mm.

The sieve itself is preferably made of metal wires. The material used may be in particular a stainless steel material, preferably alloyed with chromium and/or nickel, while more preferably the chromium content is twice as great as the nickel content, or more.

The sieve suitably consists specifically of a mesh of the above-mentioned wires. It may have a mesh size of 0.4 or more millimeters. A mesh size of 1.5 mm or less is more preferable. Still more preferable is a mesh size in the range from 0.9 to 1 mm. The specified range of 0.4-1.5 mm also includes all the intermediate values, more particularly in increments of $\frac{1}{10}$ mm from the lower and/or upper limit to the other limit. "And" here denotes that both limits are shifted towards the respective other limit, i.e. pinpointed, by one or more tenths in each case.

The wire itself may preferably have a diameter of between 0.1 and 0.5 mm, while any intermediate values, particularly in $\frac{1}{10}$ mm increments, are also included in the disclosure.

The invention further relates to a sieve part for an inhaler, particularly an inhaler in one of the embodiments as described hereinbefore, wherein the sieve part has a retaining edge and a sieve area extending in a cross-section within the retaining edge, while additionally the sieve area comprises a protruding area shaped so as to protrude to one side.

With regard to the sieve part the problem is to design this favourably for use in an inhaler, particularly a powder inhaler.

One possible solution to this problem is provided in the subject-matter of claim 11, the feature of which is that the protruding area has a flat portion. Regarding the advantages that can be achieved hereby, particularly in conjunction with a powder inhaler, reference is also made to the earlier remarks concerning the inhaler as a whole. The same also applies to the conventional aspects of the sieve part.

The invention is hereinafter explained in more detail by means of the appended drawings, although they show only one embodiment. In the drawings:

FIG. 3 shows a representation according to FIG. 2, but with a differently configured retaining edge for the sieve part;

FIG. 6 is a representation according to FIG. 4, but with a differently configured retaining edge;

Figure 1:
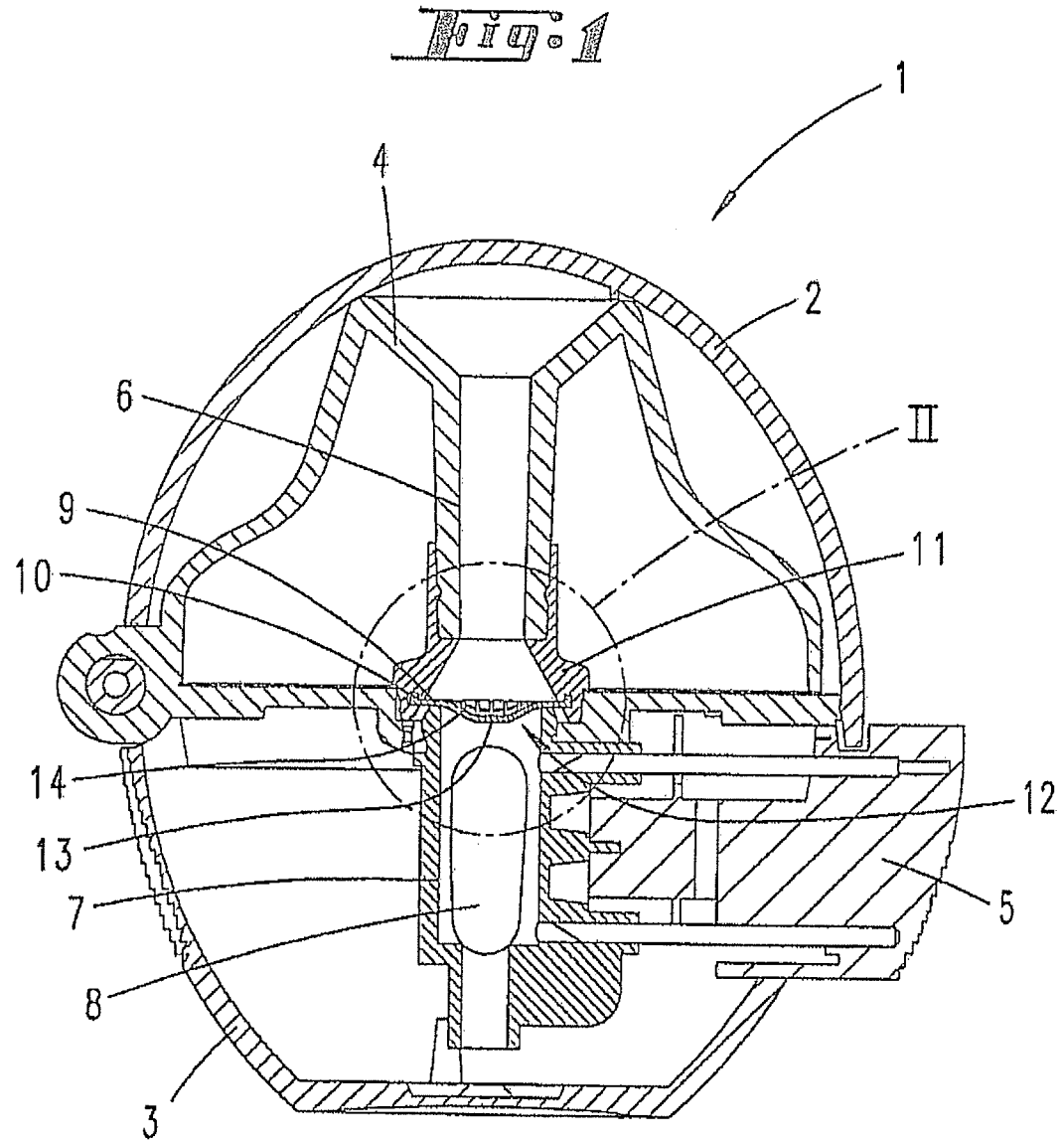
FIG. 1 shows an inhaler having a sieve arranged in the suction air channel.

Referring to FIG. 1, a powder inhaler as basically known from the previously mentioned WO 2004/062716 A1 is shown in cross-section. For further details, see the above-mentioned publication the contents of which are hereby incorporated by reference, including information as to the incorporation of features from the above-mentioned publication in a claim of the present application.

The inhaler 1 has a cover part 2, a receiving housing 3, a mouthpiece 4 and an actuating button 5.

Adjoining the mouthpiece 4 on the inside is a suction air channel 6 which merges into a receiving chamber 7 in which there is a substance supply container 8. Between the receiving chamber 7 and the suction air channel 6 is provided a sieve part 9 which is held in an adapter part 11 by means of a retaining edge 10. A free sieve area S is located within the retaining edge 10. The adapter part 11 also constitutes a part of the suction air channel 6. As is apparent particularly from FIGS. 2 and 3, the sieve part 9 has a protruding area 12 which has a flat portion 13.

The protruding area 12 is raised by a protruding amount v above the plane E that goes through the retaining edge 10 into the area in which the sieve area S merges into it. The protruding amount v corresponds to 10 to 20% of the size of a cross-sectional dimension L (viewed as a straight cross-sectional line). More preferably it corresponds to 15%. The disclosure of the specified area of 10 to 20% also includes all the intermediate values, particularly in increments of $\frac{1}{10}$%, also taking into account a narrowing of the stated range by $\frac{1}{10}$ or more percent at the bottom and/or top end.

The sieve part 9 is formed overall by a wire mesh, the cross-sectional representations in FIGS. 1 to 3 and 4, 6 each centrally intersecting a wire.

The sieve part 9 is also circular in configuration.

Figure 2:
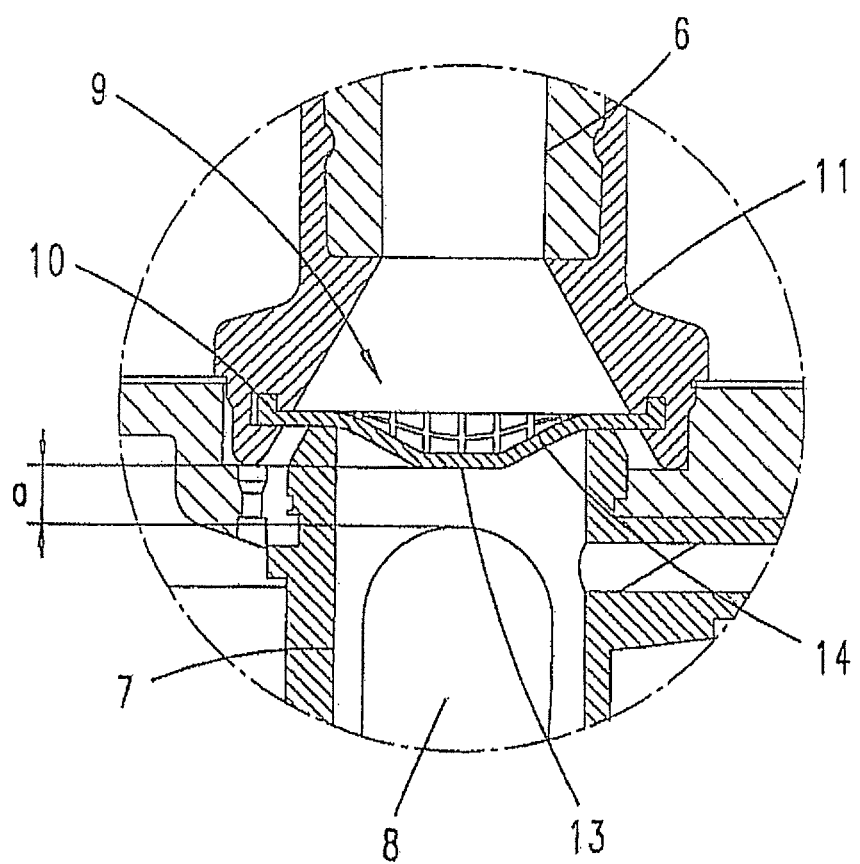
FIG. 2 shows an enlargement of the area II in FIG. 1.

As is also apparent particularly from FIGS. 2 and 3, the angled bend of the retaining edge 10 may be shaped on the one hand opposite to the clamping region 12 and on the other hand also in the direction of the convexity of the sieve part 9 provided by the protruding area 12. The retaining edge 10 may have an extrusion coating on the wire mesh, but may also be formed purely by the wire mesh itself.

For correct operation of the inhaler it is essential that the distance a, cf. FIG. 3, for example, is very precisely defined between an upper end of the unmoved substance supply container 8 located in a starting position and the closest area at that stage, namely the flat portion 13 of the sieve part 9, and can also be very accurately maintained in view of the manufacturing tolerances, particularly of the sieve part 9. This is ensured by the flat portion 13. The objective is a dimensional tolerance that corresponds to half, or less, of the thickness of the wire in the sieve part 9.

Moreover, in the event of contact between the substance supply container 8 and the sieve part 9, the resulting increase in stability of the design ensures that there is also a reduced negative impact on the dimensional stability.

Figure 4A:
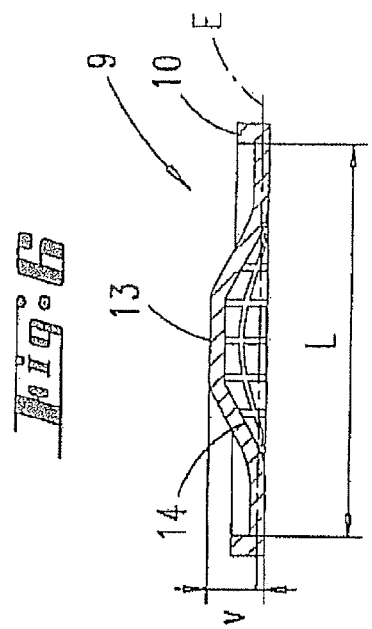
FIG. 4 shows a cross-section through the sieve part on its own.
Figure 4B:
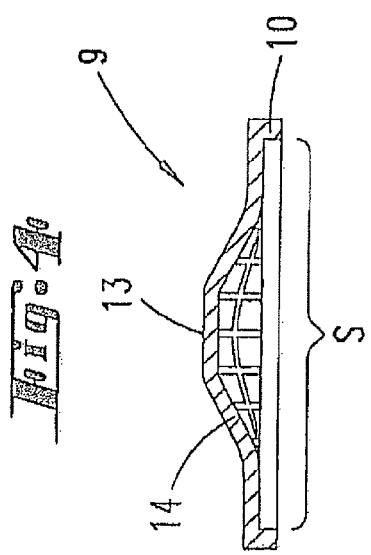

As can be seen in more detail in FIGS. 4 and 6, adjoining the flat portion 13 radially outwardly is a substantially straight transitional region 14 which is provided circumferentially to correspond to the basic circular shape of the sieve part 9 and is hence conical in shape.

Figure 5:
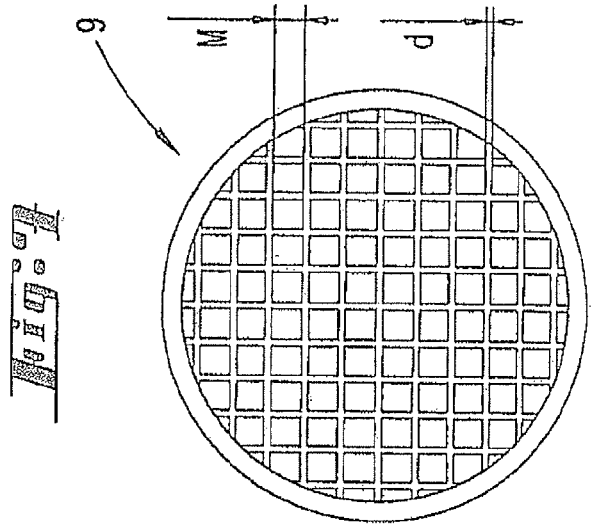
FIG. 5 shows a plan view of the sieve part according to FIG. 4 viewed from above.
Figure 7:
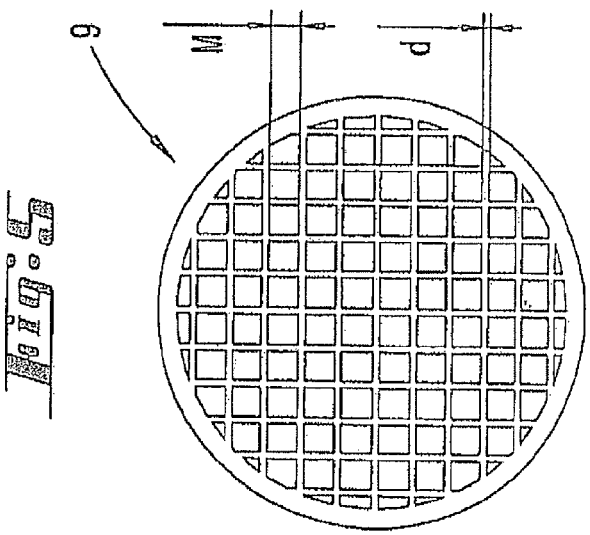
FIG. 7 is a plan view of the object of FIG. 6, viewed from above.

The mesh size M, as explained with reference to FIG. 5 or 7, is 0.8 mm, while the thickness d of a wire as used for the sieve mesh is 0.25 mm.

All the features disclosed are of themselves essential to the invention. The disclosure of the application also includes by reference the entire contents of the disclosure of the associated/enclosed priority documents (copy of the original application), with the purpose of incorporating features from these documents in claims in the present application.

The invention claimed is:

1. An inhaler (1) for powdered medicinal substances, comprising:
   a suction air channel (6) leading to a mouthpiece (4),
   a substance supply container (8) movably arranged in a receiving chamber (7), and
   a sieve part (9) disposed in the suction air channel (6) between the receiving chamber (7) and the mouthpiece (4), said sieve part having a retaining edge (10) and a sieve area circumscribed by the retaining edge (10), wherein the sieve area comprises a convex protruding area (12) shaped to protrude from a plane in which the retaining edge is located and toward the substance supply container (8), and wherein the protruding area (12) has a flat portion (13) at an apex thereof wherein the flat portion comprises 5% or more of the sieve area extending within the retaining edge.

2. The inhaler according to claim 1, wherein the protruding area (12), viewed in cross-section, projects over the retaining edge (10) at right-angles to the plane in which the retaining edge is disposed.

3. The inhaler according to claim 1, wherein the flat portion (13) is central with respect to the sieve area, viewed in cross-section.

4. The inhaler according to claim 1, wherein the sieve area or the sieve part (9) as a whole is made of metal wires.

5. The inhaler according to claim 1, wherein the sieve area or the sieve part (9) as a whole includes a wire mesh.

6. The inhaler according to claim 5, wherein the sieve area has a mesh size of 0.4 mm or more.

7. The inhaler according to claim 5, wherein the sieve area has a mesh size of 1 mm or less.

8. The inhaler according to claim 5, wherein the sieve area has a mesh size of 0.6 to 1.0 mm or less.

9. The inhaler according to claim 5, wherein the wires have diameters of between 0.1 and 0.5 mm.

10. A sieve part (9) for an inhaler (1) for powdered medical substances, comprising:
    a retaining edge (10) located within a plane; and
    a sieve area circumscribed by the retaining edge (10), and including a convex protruding area (12) shaped to protrude from the plane in which the retaining edge is located, wherein the protruding area (12) has a flat portion (13) at an apex thereof.

11. A sieve part (9) for an inhaler for powdered medical substances, comprising:
    a retaining edge (10) located in a plane and defining a diameter dimension;
    an angular bend extending away from the retaining edge and out of the plane in one direction; and
    a sieve area circumscribed by the retaining edge (10) and including a convex protruding area (12) shaped to protrude from the plane in which the retaining edge is located to an apex, thereby defining a height dimension, wherein the height is between 10-20% of the diameter dimension, and wherein the protruding area (12) has a flat portion (13) at an apex thereof wherein the flat portion comprises 5% or more of the sieve area extending within the retaining edge.

12. The sieve part (9) according to claim 11, wherein the bend is formed by an outermost edge portion of the sieve part (9).

13. The sieve part (9) according to claim 11, wherein the protruding area (12) and the angular bend extend in opposite directions.

14. The sieve part (9) according to claim 11, wherein the protruding area (12) and the angular bend extend in a same direction.

15. The sieve part (9) according to claim 11, wherein the sieve part (9) is made as a whole from a flat wire mesh part by bending or deep drawing, with at least partial plastic deformation.

16. The sieve part (9) according to claim 11, wherein the sieve part (9) is made from a wire mesh part and the retaining edge (10) is purely formed by the wire mesh itself.

17. The sieve part (9) according to claim 11, wherein the sieve part (9) is made from a wire mesh part and the retaining edge (10) has an extrusion coating on the wire mesh.

18. The sieve part (9) according to claim 11, wherein the sieve part (9) is circular in configuration and the sieve area comprises a protruding area (12) providing convexity to the sieve part (9).

19. The inhaler (1) of claim 1, wherein the convex protruding area (12) is in the form of a dome-shaped region having the flat portion (13) centrally located at an apex thereof.

20. The inhaler (1) of claim 1, wherein the convex protruding area (12) is in the form of conical-shaped region having the flat portion (13) centrally located at an apex thereof.

21. An inhaler (1) for powdered medicinal substances, comprising:
    a suction air channel (6) leading to a mouthpiece (4);
    a substance supply container (8) movably arranged in a receiving chamber (7); and
    a sieve part (9) disposed in the suction air channel (6) between the receiving chamber (7) and the mouthpiece (4), said sieve part having a retaining edge (10), a sieve area circumscribed by the retaining edge (10), a convex protruding area (12) shaped to protrude from a plane in which the retaining edge is located and toward the substance supply container (8), and a flat portion (13) at an apex of the protruding area (12), wherein the flat portion (13) comprises between 5% and 15% of the sieve area extending within the retaining edge (10).

22. The sieve part (9) of claim 10, wherein:
the retaining edge (10) defines diameter dimension; and
the convex protruding area (12) protrudes to the apex, thereby defining a height dimension, wherein the height is between 10-20% of the diameter dimension.

* * * * *